United States Patent [19]
Murase

[11] Patent Number: 5,583,299
[45] Date of Patent: Dec. 10, 1996

[54] CONDUIT FOR AN ELECTROMAGNETIC FLOWMETER USING MAGNETIC POLES AS GROUND ELECTRODES

[75] Inventor: Nobuyasu Murase, Nagoya, Japan

[73] Assignee: Aichi Tokei Denki Co., Ltd., Aichi-ken, Japan

[21] Appl. No.: 492,150

[22] Filed: Jun. 19, 1995

[30] Foreign Application Priority Data

Jun. 20, 1994 [JP] Japan .................................. 6-136193

[51] Int. Cl.$^6$ .................................................. G01F 1/58
[52] U.S. Cl. .................................. 73/861.12; 73/861.13
[58] Field of Search ................................ 73/861, 861.11, 73/861.12, 861.08, 861.13

[56] References Cited

U.S. PATENT DOCUMENTS

| | | |
|---|---|---|
| 2,149,847 | 3/1939 | Kolin . |
| 2,766,621 | 10/1956 | Raynsford ........................... 73/861.12 |
| 3,309,924 | 3/1967 | Kolin et al. ......................... 73/861.12 |
| 4,118,981 | 10/1978 | Cave . |
| 4,195,515 | 4/1980 | Smoll . |
| 4,454,766 | 6/1984 | Reinhold et al. .................... 73/861.12 |
| 4,881,413 | 11/1989 | Georgi et al. . |
| 5,213,765 | 5/1993 | Kasai et al. ........................... 422/101 |
| 5,325,728 | 7/1994 | Zimmerman et al. ............... 73/861.11 |

FOREIGN PATENT DOCUMENTS

| | | |
|---|---|---|
| 459480 | 5/1991 | European Pat. Off. . |
| 39-29490 | 11/1964 | Japan . |
| 4-324321 | 11/1992 | Japan . |
| 4-324320 | 11/1992 | Japan . |
| 2160658 | 6/1985 | United Kingdom . |

*Primary Examiner*—Richard Chilcot
*Assistant Examiner*—Max H. Noori
*Attorney, Agent, or Firm*—Pollock, Vande Sande & Priddy

[57] ABSTRACT

A pair of electrodes and a pair of magnetic poles are mounted to a resin-made conduit body with each of those parts partly exposed to the lumen. The magnetic poles are formed by an electrically conductive material and serve also as ground electrodes by being connected to ground. The magnetic poles serving also as the ground electrodes are positioned in the same plane as signal electrodes with a result that the distance on the axis of the conduit between the signal electrodes and the ground electrodes is fixed, more precisely, the distance is zero, so that the zero point of the electromagnetic flowmeter is stabilized. The magnetic poles, mounted to the conduit body, are separated from the yokes on which coils are wound, and both the magnetic poles and the yokes are detachable.

16 Claims, 6 Drawing Sheets

CONDUIT FOR AN ELECTROMAGNETIC FLOWMETER USING MAGNETIC POLES AS GROUND ELECTRODES

BACKGROUND OF THE INVENTION

This invention relates to an electromagnetic flowmeter.

The use of an electromagnetic flowmeter designed with sanitary considerations in mind, i.e., to measure the flow rate of blood is well known. The basic concept is described in U.S. Pat. No. 2,149,847, for example.

Electromagnetic flowmeters using a disposable conduit for passing blood therethrough, are disclosed in U.S. Pat. Nos. 4,118,981, 4,195,515, 4,881,413 and JP-A-4 (1992)-324320.

The conduit includes a conduit body made of resin, a pair of signal receiving electrodes, and a pair of ground electrodes, arranged along the lumen of the conduit body at a specified distance from the pair of signal electrodes.

SUMMARY OF THE INVENTION

The present invention improves the prior-art flowmeters with respect to the following problem.

According to the conduit described in U.S. Pat. No. 4,881,413, there is a possibility that the dimensions of the conduit body change depending on the manufacturing condition and temperature changes, etc. Errors are likely to occur in the distance on the axis of the lumen between the signal electrodes and the ground electrodes. Such an error causes a shifting of the zero point of the electromagnetic flowmeter.

In the disposable conduit disclosed in the prior art, a pair of magnetic poles for the application of a magnetic field to the lumen are inserted into the conduit body from outside, so that there invariably exists the material of the conduit body between the lumen and the poles of the electromagnet. In other words, since the material of the conduit body is included in the magnetic circuit, the magnetic reluctance of the magnetic circuit is made unnecessarily large.

The object of the present invention is to solve at least one of the above-mentioned problems.

According to an aspect of the present invention, the pair of the poles of the electromagnet are each partly exposed to the lumen. To reduce the resistance of the lumen, the exposed portions preferably terminate flush with the surface of the lumen. By this arrangement, the unnecessary magnetic reluctance is removed from the magnetic circuit. The magnetic efficiency is improved and, in addition, electric power required for the electromagnet is decreased.

If at least one of the pair of magnetic poles is formed by an electrically conductive material connected to a ground potential, this magnetic pole serves also as the ground electrode. Thus, a separate ground electrode which is typically needed in the prior art devices can be omitted in the present invention. By arranging the magnetic poles and the electrodes substantially in the same plane, the distance between the signal electrodes and the ground electrodes is substantially constant, i.e., fixed more precisely, the distance is zero, and for this reason, the zero point of the electromagnetic flowmeter is stabilized.

The pair of magnetic poles arranged as described are positioned closely to each other, and accordingly the magnetic flux density distribution in the lumen becomes advantageous, making it possible to measure the flow rate with high accuracy.

According to the present invention, the magnetic poles are exposed to the lumen, and to secure the sealability between the magnetic poles and the conduit body, the magnetic poles are inserted with high air-tightness. Therefore, the magnetic poles are made as discrete components to form a magnetic path, which are separate from other magnetic-path components, such as the yokes in the clamp holding the conduit. Thus, the magnetic poles and the yokes are detachable. In order to readily connect the yokes and the magnetic poles, one end of each magnetic pole is formed in a circular cone which protrudes from the conduit body, while a cavity is formed in the yoke to receive the protruding cone.

Another object of the present invention is to improve the accuracy of measurement. To this end, the yokes are formed by an electrically conductive and magnetic material. Under the condition that the conduit is mounted in the clamp, that is, the conduit is held by the clamp, the electrodes and the magnetic poles are enclosed by the yokes. Thus, electrodes for acquiring signals, electrodes for providing ground potential and leads therefrom are shielded from outer electrostatic noise and electromagnetic noise.

In another aspect, the present invention includes a method of manufacturing a conduit for passing blood therethrough. A conduit body is formed and then a film of anticoagulant is formed on the surface of the lumen.

The molding material of the conduit body does not have to be specified if it is electrically insulating, and a manufacturing method may be freely selected according to the kind of molding material. For example, if the conduit body is molded out of a resin, injection molding, compression molding or the like is selected. In molding the conduit body, holes into which the electrodes and the magnetic poles are inserted are formed at the same time. It is also possible to form a tubular material by extrusion molding, cut the tubular material into conduit bodies with an adequate, uniform length, and subsequently bore the holes in the conduit bodies.

The film of anticoagulant is formed by immersing the conduit body in an anticoagulant, or applying or spraying an anticoagulant to the conduit body or by using any other known method.

Subsequently, the electrodes and the magnetic poles coated with an adhesive, are force-fitted into the holes of the conduit body to thereby secure the sealability between the conduit body and the electrodes and magnetic poles. The anticoagulant film does not exist on the surfaces of the electrodes and magnetic poles which are exposed to the lumen. Therefore, the impedance between the fluid flowing through the lumen, and the electrodes and the magnetic poles serving as the ground electrodes is not affected by the anticoagulant. Needless to say, since the areas of the exposed surfaces of the electrodes and the magnetic poles are very small, even though they are not covered with the anticoagulant, they have hardly any influence on the blood.

When the film of anticoagulant is formed on the walls of the lumen after the electrodes and magnetic poles have been mounted on the conduit body, it is necessary to prevent the film from being formed on the surfaces of the electrodes and magnetic poles exposed to the lumen. For example, the anticoagulant is dissolved in a solvent medium which has an extremely poor wettability to the molding material of the electrodes and magnetic poles, but has a good wettability to the walls of the lumen. Then the anticoagulant is applied to the walls of the lumen.

BRIEF DESCRIPTION OF THE DRAWINGS

These and other objects and technical advantages of the present invention will be readily apparent from the following description of the preferred exemplary embodiments of the invention in conjunction with the accompanying drawings, in which.

DESCRIPTION OF THE PREFERRED EMBODIMENTS

Figure 1A:
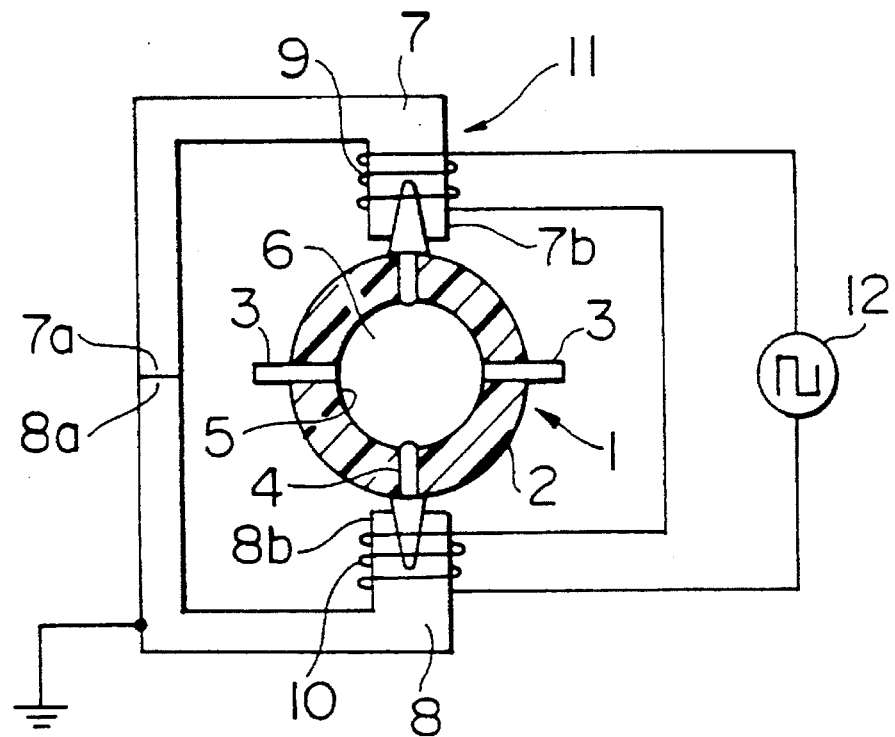
FIG. 1A is a diagram showing the construction of the electromagnetic flowmeter according to an embodiment of the present invention.
Figure 1B:
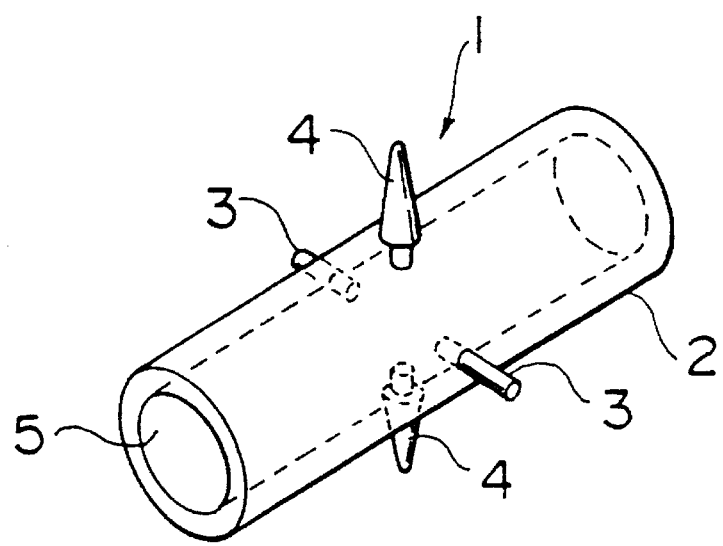
FIG. 1B is a perspective view of the conduit according to the embodiment.

In FIGS. 1A and 1B, reference numeral 1 denotes a conduit including a conduit body 2 formed by a plastic material, a pair of signal electrodes 3 inserted into the conduit body 2, and a pair of magnetic poles 4 inserted into the conduit body 2 and serving also as ground electrodes.

The conduit body 2 has a lumen 5 of a circular cross section passing in the longitudinal direction thereof. Reference numeral 6 denotes a lumen flow path to which the signal electrodes 3 are exposed. The axis of the lumen 5, the axial direction of the signal electrodes 3 and the axial direction of the magnetic poles 4 serving also as the ground electrodes are mutually perpendicular to each other.

Reference numerals 7, 8 denote L-shaped magnetic cores having coils 9, 10 respectively wound thereon. The cores 7, 8 and coils 9, 10 form excitation means 11. The cores 7, 8 are connected with one-end portions 7a, 8a thereof put together, and the magnetic poles 4 are fitted in the cavities at the other-end portions 7b, 8b.

The extreme ends of the magnetic cores 4 are exposed to the lumen 5 (the lumen flow path 6 passing through the conduit body) and directly in contact with a fluid, such as blood flowing through the lumen 5 (the lumen flow path 6). The lumen flow path 6 has a circular cross-section, and the extreme ends of the magnetic cores 4 are tapered to each form a circular cone.

Reference numeral 12 denotes an exciting power source to supply a square wave current for energizing the coils 9, 10.

Figure 2:
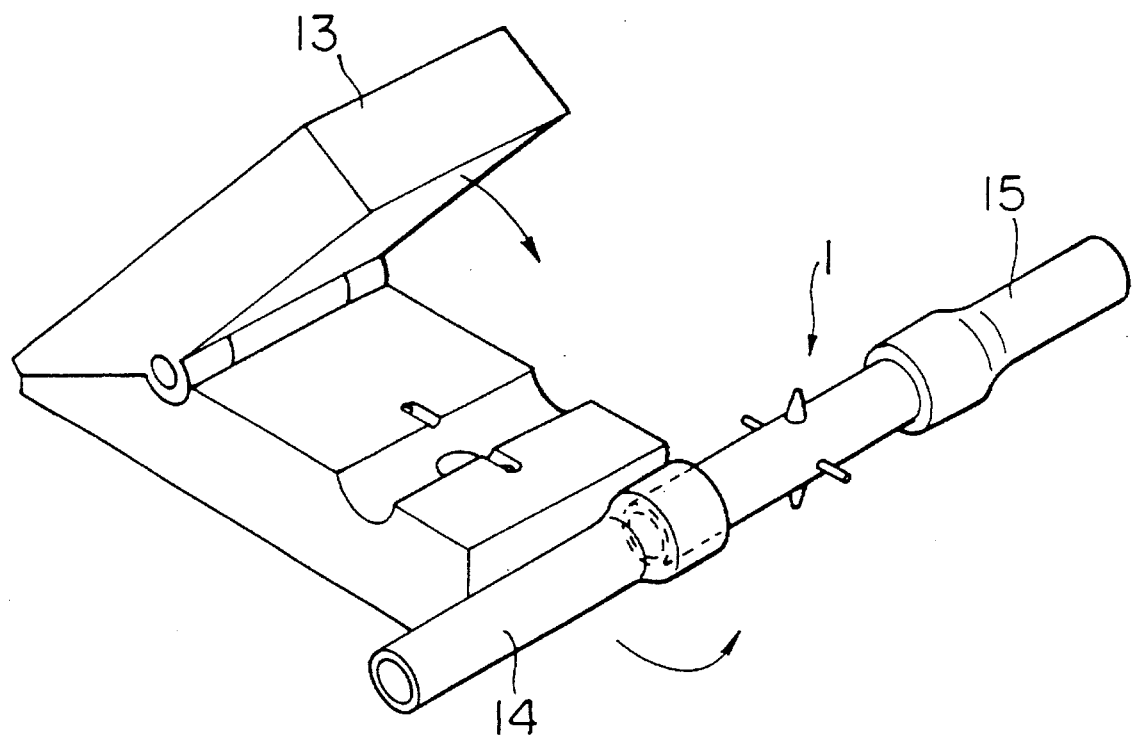
FIG. 2 is a perspective view showing the conduit and the clamp for holding the conduit.

FIG. 2 shows how a conduit 1 having hoses 14, 15 attached thereto is mounted in a clamp 13 of the same construction that of the clamp disclosed in JP-A-4-324320, by opening this clamp 13. The clamp 13 has the excitation means 11, shown in FIG. 1A, mounted therein, and when the clamp 13 is opened as shown in FIG. 2, the cores 7 and 8 are opened. Under this condition, the conduit 1 is inserted into a predetermined position of the clamp 13, and then the clamp 13 is closed. Thus, the conduit 1 is held with the magnetic poles 4, which also serve as the ground electrodes, secured between the end-portions 7b, 8b of the cores 7 and 8 as shown in FIG. 1A.

In this holding condition, there is no clearance between the end potions 7b, 8b of the cores 7, 8, and the only empty space for the magnetic path lies in the lumen flow path 6.

A magnetic field is generated in the lumen flow path 6 by an electromagnet formed by the cores 7, 8, the coils 9, 10 and the magnetic poles 4.

A voltage signal is generated between the signal electrodes 3 which is proportional to the flow rate of a fluid flowing through the lumen 5. By processing this voltage signal by an electronic circuit, the flow rate is computed. The processing is shown, for example, in JP-B 39-29490, U.S. Pat. Nos. 4,118,981, 4,195,515 and 4,881,413. The contents thereof are incorporated herein by reference.

Figure 3:
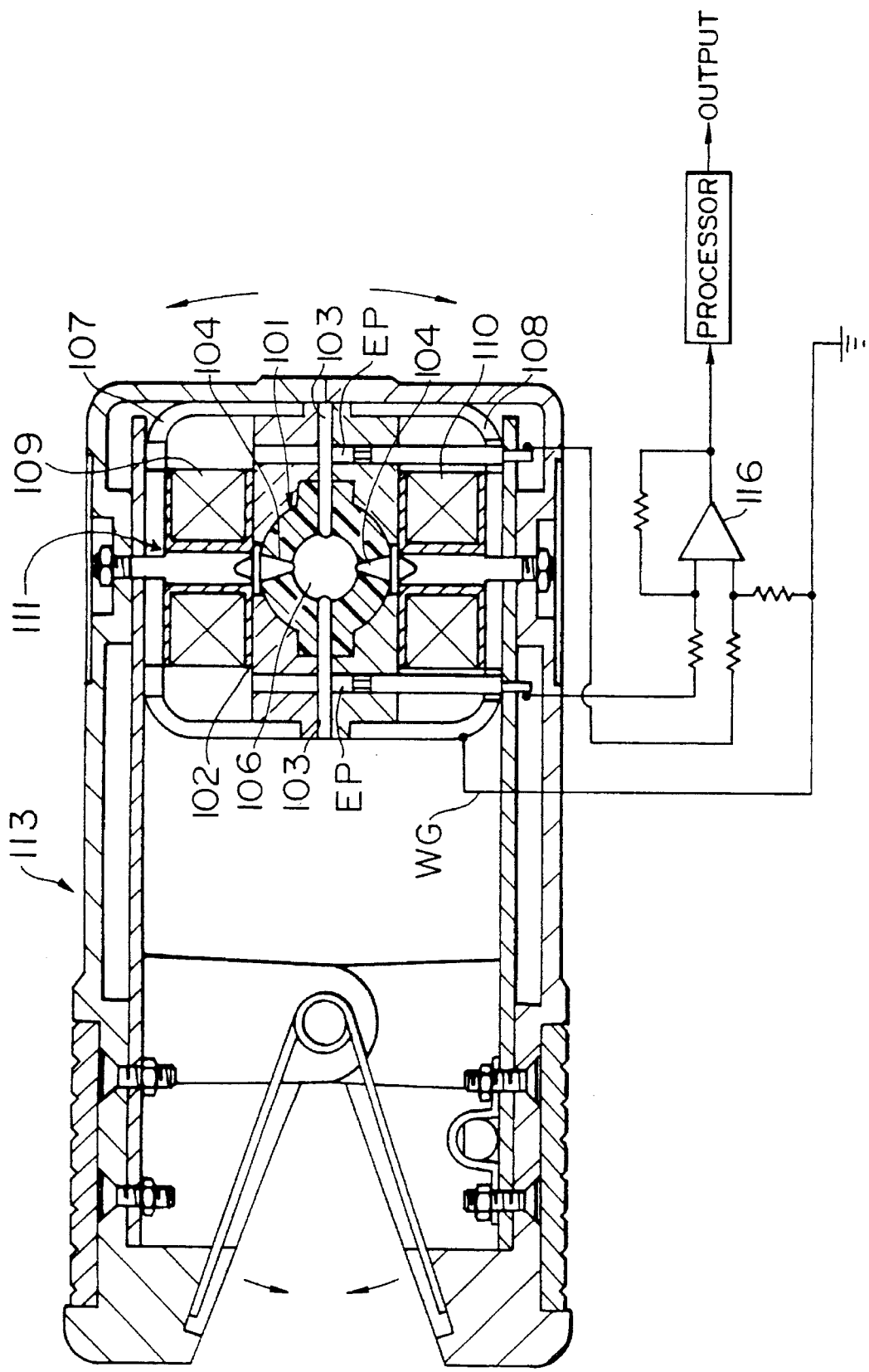
FIG. 3 is a diagram showing the construction of the electromagnetic flowmeter according to another embodiment of the present invention.

FIG. 3 is a sectional view of the electromagnetic flowmeter according to another embodiment of the present invention. The sectional view shows the condition in which the clamp 13 is closed. In FIG. 3, the magnetic cores 107, 108 of the excitation means 111 are E-shaped in cross section in contrast to the L-shaped cores in FIG. 1A. There is no difference in the essential function of applying a magnetic field to the lumen between the L-shaped cores in FIG. 1A and the E-shaped cores in FIG. 3. However, the L-shaped cores 7, 8 surround the electrode 3 only on one side, whereas the E-shaped cores 107, 108 surround the two electrodes 103. To provide an electrical ground, the cores 107, 108 are in contact with a fluid, and this arrangement offers a shield effect against electromagnetic or electrostatic noise which may otherwise enter from outside. The shield effect is superior in the example in FIG. 3, which covers the electrodes 103 on both sides.

The symbols EP denote contacts to pick up electromotive forces on the signal electrodes 103. WG denotes a grounding wire to couple the core 108 to the ground terminal of the differential amplifier 116.

In the above embodiment, the conduit body 101 is formed by polycarbonate. The electrodes 103 are formed by austenitic stainless steel (type: SUS 316L) which is an antimagnetic material. The magnetic poles 104 and yokes 107, 108 are formed by a ferritic stainless steel (type: SUS 430) which is a magnetic and electrically conductive material. A thin layer of anticoagulant, such as heparin or material of organism which is substantially similar to that of blood vessel, is formed on the surface of the lumen of the conduit body 101 to a thickness of about several microns. Needless to say, the yoke 108 is isolated from the electrodes 103 and the contact EP.

Figure 4:
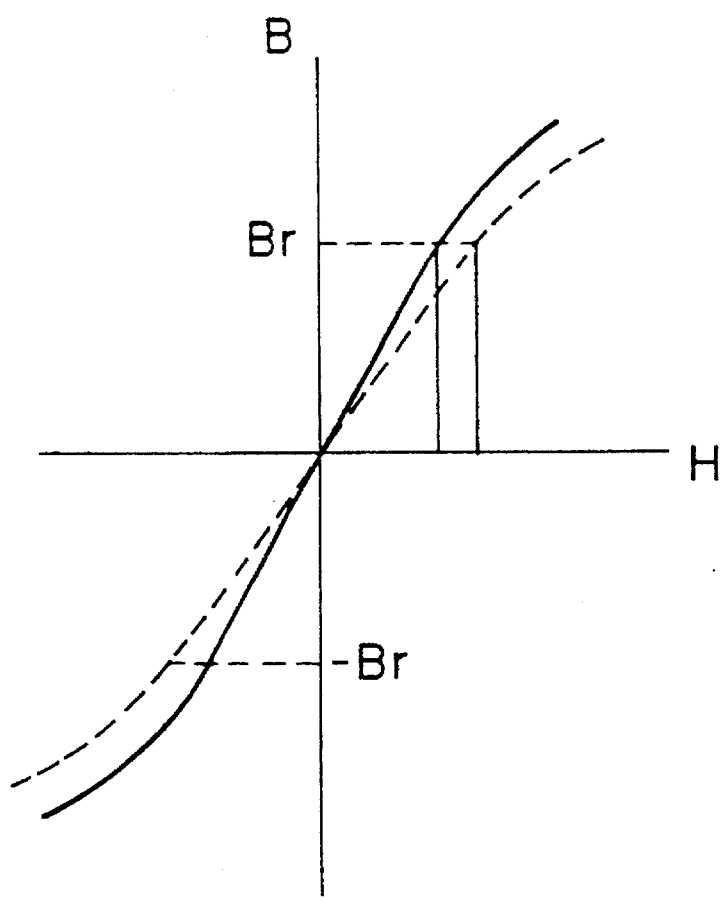
FIG. 4 is a graph comparing B-H characteristics of the embodiment and the prior art.

In the above embodiment, since the lumen flow path 6 is the only empty space of the electromagnet, as shown in FIG. 4, the excitation energy H required to generate a magnetic field with a flux density of Br in the lumen flow path 6 is smaller than in the prior art, which means a better excitation efficiency. In FIG. 4, the solid line indicates the curve in this embodiment, while the dotted line indicates the curve in the prior art.

Figure 5A:
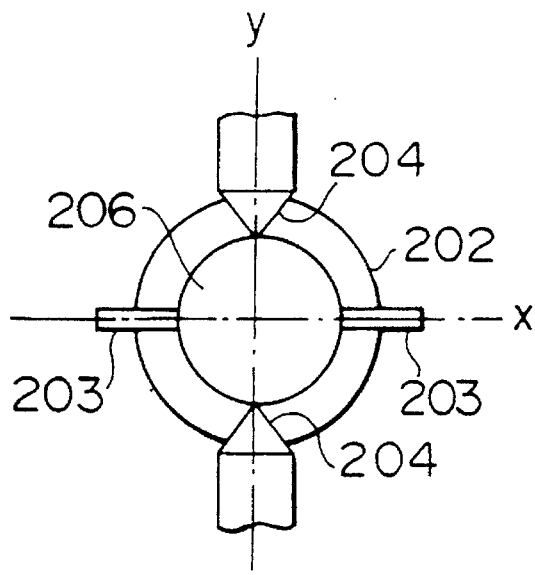
FIG. 5A is a diagram showing the conduit according to another embodiment.
Figure 5B:
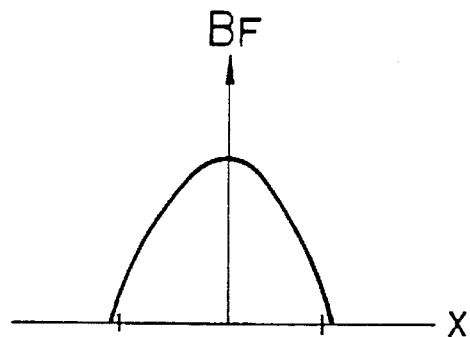
FIG. 5B is a graph showing the magnetic flux density in the conduit.
Figure 5C:
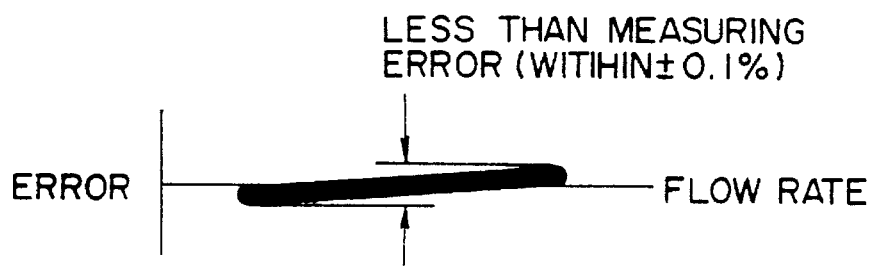
FIG. 5C is a graph showing the error characteristics of the electromagnetic flowmeter according to the embodiment.

As shown in FIGS. 5A and 5B, the distribution curve for the magnetic flux density $B_F$ along the axis connecting the signal electrodes 203 centers round the y-axis. In consequence, as shown in FIG. 5C, the flow rate characteristics have been improved and the errors could be contained within the measuring error of ±0.1% for a wide range of flow rates.

Because the ground electrodes are formed by the magnetic poles 204 and the y-axis of the magnetic poles 204 serving also as the ground electrodes lies in a plane which contains the x-axis of the signal electrodes 203 and which is at right angles to the axis of the lumen 205, the distance on the axis of the lumen 205 between the signal electrodes 203 and the ground electrodes (in other words, the magnetic poles 204) is never changed by distortion which occurs when the conduit body 202 is formed by a plastic material. As a result the shifting or variation of zero point which occurs in the prior art can be prevented. Therefore, even when the conduit 201 is produced as a disposable part which is discarded after each surgical procedure, it is unnecessary to inspect the zero point for each conduit in mass-production of the conduits 201, so that the inspection manpower can be saved and the production cost can be reduced accordingly.

The electromagnetic flowmeter and the conduit according to the present invention are constructed as described, so that costs of material and parts can be decreased and the magnetic efficiency can be improved. Because it is possible to prevent the shifting or variation of the zero point caused by distortion which occurs in forming the conduit, the inspection manpower can be saved. The above-mentioned advantages are particularly notable with the parts which need to be produced at low cost, such as disposable conduits.

The magnetic flux density can be obtained in an improved distribution in the lumen flow path where the electrodes and the magnetic poles are arranged. The flow rate characteristics are therefore enhanced.

Figure 6:
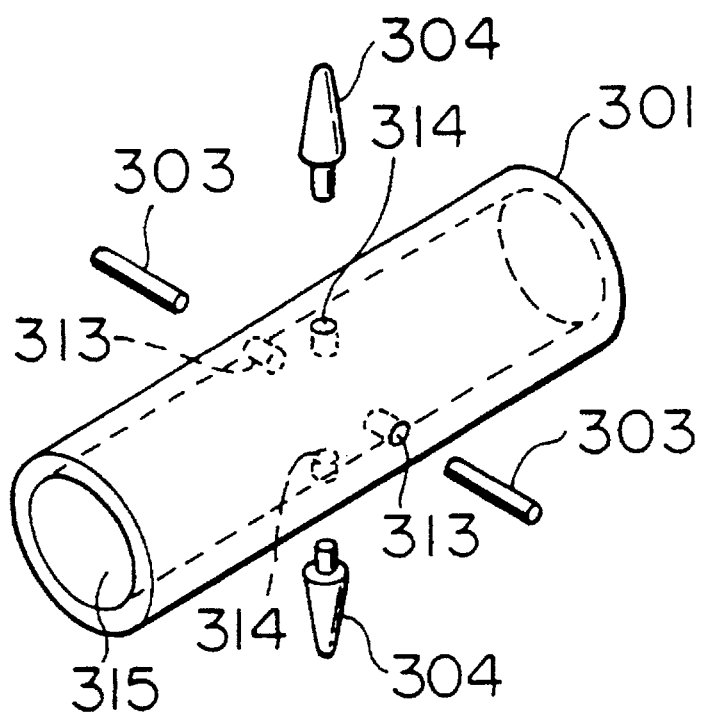
FIG. 6 is an exploded perspective view of the conduit according to the embodiment for explaining the method of manufacturing the conduit.

The manufacturing method of the conduit will now be described with reference to FIG. 6.

At first, a conduit body is molded. In this molding process, holes 313 and 314 into which the electrodes 303 and the magnetic poles 304 are to be inserted are formed. Diameters of holes are a little smaller than that of respective poles.

A layer of anticoagulant is formed on the lumen surface 315 of the conduit body 303. Then, the electrodes 303 and the magnetic poles 304, are press-fitted into the holes 313 and 314, by which the conduit body is formed. A metal-resin adhesive, such as Araldite (trade name) provided by Ciba-Geigy Corp., may be interposed between walls of the holes and the poles.

Although the present invention has been described in detail, it should be understood that various changes, substitutions and alterations can be made hereto without departing from the spirit and scope of the present invention as defined by the appended claims.

What is claimed is:

1. A conduit for an electromagnetic flowmeter, said conduit comprising:

a conduit body having a lumen extending therethrough for passing fluid;

a pair of signal electrodes attached to said conduit body such that said pair of signal electrodes is orthogonal to a longitudinal axis of said lumen and partially exposed to said lumen; and a pair of magnetic poles attached to said conduit body such that said pair of magnetic poles is orthogonal to said longitudinal axis of said lumen and to said pair of signal electrodes and positioned substantially in the same plane as said pair of signal electrodes, said pair of magnetic poles being partially exposed to said lumen and being made from an electrically conductive material, and at least one magnetic pole of said pair of magnetic poles being connected to ground potential, whereby said pair of magnetic poles serve as ground electrodes and wherein said conduit is disposable.

2. The conduit according to claim 1, wherein each pole of said pair of magnetic poles has a portion protruding from said conduit body for coupling to yokes.

3. The conduit according to claim 2, wherein said protruding portion has a guided surface for positioning said each magnetic pole relative to said yokes when said pair of magnetic poles is coupled to said yokes.

4. The conduit according to claim 3, wherein said protruding portion is conical in shape and has a tapered surface to serve as said guided surface.

5. An electromagnetic flowmeter, comprising:

a disposable conduit which includes (a) a conduit body having a lumen extending therethrough for passing fluid; (b) a pair of signal electrodes attached to said conduit body such that said pair of signal electrodes is orthogonal to a longitudinal axis of said lumen and partially exposed to said lumen; and (c) a pair of magnetic poles attached to said conduit body such that said pair of magnetic poles is orthogonal to said longitudinal axis of said lumen and to said pair of signal electrodes and positioned substantially in the same plane as said pair of signal electrodes, said pair of magnetic poles being partially exposed to said lumen and being made from an electrically conductive material, and at least one magnetic pole of said pair of magnetic poles being connected to ground potential, whereby said pair of magnetic poles serve as ground electrodes and wherein said conduit is disposable;

holding means for holding said disposable conduit;

means for applying a magnetic field to said lumen including yokes connected to said pair of magnetic poles and an electromagnet, wherein said yokes and said electromagnet are mounted in said holding means; and means for computing a flow rate of fluid passing through said lumen by processing a signal obtained from said pair of signal electrodes.

6. The electromagnetic flowmeter according to claim 5, wherein said at least one magnetic pole is grounded through said yokes.

7. The electromagnetic flowmeter according to claim 5, wherein each pole of said pair of magnetic poles has a portion protruding from said conduit body, and each yoke has a cavity for fitting said protruding portion therein, whereby said magnetic poles and said yokes can be separated.

8. The electromagnetic flowmeter according to claim 7, wherein said protruding portion and said cavity each has a guided surface, wherein said pair of magnetic poles are coupled to said yokes via said guided surfaces.

9. The electromagnetic flowmeter according to claim 8, wherein said protruding portion is conical in shape and has a tapered surface which serves as said guided surface.

10. The electromagnetic flowmeter according to claim 5, wherein said yokes are electrically conductive and grounded, and enclose said conduit for shielding from electrostatic and electromagnetic noise.

11. A clamp for holding a disposable conduit in an electromagnetic flowmeter, comprising:

a conduit body having a lumen extending therethrough for passing fluid;

a pair of signal electrodes attached to said conduit body such that said pair of signal electrodes is orthogonal to a longitudinal axis of said lumen and partially exposed to said lumen;

a pair of magnetic poles attached to said conduit body such that said pair of magnetic poles is orthogonal to said longitudinal axis of said lumen and to said pair of signal electrodes and positioned substantially in the same plane as said pair of signal electrodes, said pair of magnetic poles being partially exposed to said lumen and being made from an electrically conductive material, and at least one magnetic pole of said pair of magnetic poles being connected to ground potential and having a protruding portion, whereby said pair of magnetic poles serve as ground electrodes and wherein said conduit is disposable;

a pair of yokes connected to said pair of magnetic poles, wherein each yoke of said pair has a cavity for fitting said protruding portion therein; and an electromagnet.

12. The clamp according to claim 11, wherein said yokes are electrically conductive and grounded.

13. The clamp according to claim 11, wherein said yokes enclose said conduit for shielding from electrostatic and electromagnetic noise.

14. A conduit for an electromagnetic flowmeter, said conduit comprising:

a conduit body having a lumen extending therethrough for passing fluid;

a pair of signal electrodes attached to said conduit body such that said pair of signal electrodes is orthogonal to a longitudinal axis of said lumen and partially exposed to said lumen;

a pair of magnetic poles attached to said conduit body such that said pair of magnetic poles is orthogonal to said longitudinal axis of said lumen and to said pair of signal electrodes and positioned substantially in the same plane as said pair of signal electrodes, said pair of magnetic poles being partially exposed to said lumen and being made from an electrically conductive material, and at least one magnetic pole of said pair of magnetic poles being connected to ground potential, whereby said pair of magnetic poles serve as ground electrodes and wherein said conduit is disposable; and a layer of anticoagulant formed on a surface of said lumen in said conduit body, except for areas of said pair of electrodes and said pair of magnetic poles which are exposed to said lumen.

15. An electromagnetic flowmeter, comprising:

a conduit body having a lumen extending therethrough for passing fluid;

a pair of signal electrodes attached to said conduit body such that said pair of signal electrodes is orthogonal to a longitudinal axis of said lumen and partially exposed to said lumen;

means for applying a magnetic field to said lumen including (a) a pair of magnetic poles attached to said conduit body such that said pair of magnetic poles is orthogonal to said longitudinal axis of said lumen and to said pair of signal electrodes and positioned substantially in the same plane as said pair of signal electrodes, said pair of magnetic poles being partially exposed to said lumen and being made from an electrically conductive material, and at least one magnetic pole of said pair of magnetic poles being connected to ground potential, whereby said pair of magnetic poles serve as ground electrodes and wherein said conduit is disposable; (b) yokes connected to said pair of magnetic poles; (c) an electromagnet; and means for computing a flow rate of a fluid flowing through said lumen by processing a signal obtained by said pair of electrodes.

16. The electromagnetic flowmeter according to claim 15, wherein said pair of magnetic poles and said yokes are formed from an electrically conductive material for connecting fluid passing through said lumen to ground.

\* \* \* \* \*